United States Patent
Andrews et al.

(10) Patent No.: US 8,663,709 B1
(45) Date of Patent: Mar. 4, 2014

(54) COMPOSITION AND METHOD FOR FERTILITY THERAPY USING NUTRITIONAL SUPPLEMENTS

(75) Inventors: Kelly Andrews, Bellingham, WA (US); Amos N Grunebaum, New York, NY (US)

(73) Assignee: Fairhaven Health, LLC, Bellingham, WA (US)

( * ) Notice: Subject to any disclaimer, the term of this patent is extended or adjusted under 35 U.S.C. 154(b) by 0 days.

(21) Appl. No.: 12/769,618

(22) Filed: Apr. 28, 2010

Related U.S. Application Data

(63) Continuation-in-part of application No. 12/551,465, filed on Aug. 31, 2009, now Pat. No. 8,383,165.

(51) Int. Cl.
*A61K 36/00* (2006.01)
*A61K 36/87* (2006.01)
*A61K 36/25* (2006.01)

(52) U.S. Cl.
USPC .......................... 424/725; 424/766; 424/728

(58) Field of Classification Search
None
See application file for complete search history.

(56) References Cited

U.S. PATENT DOCUMENTS

| | | | |
|---|---|---|---|
| 6,235,784 B1 * | 5/2001 | Cavazza | 514/561 |
| 2006/0154993 A1 * | 7/2006 | Littarru et al. | 514/690 |
| 2007/0104801 A1 * | 5/2007 | Cecchi et al. | 424/641 |
| 2007/0116786 A1 * | 5/2007 | Zheng et al. | 424/725 |
| 2009/0280203 A1 * | 11/2009 | Gonzales Rengifo et al. | 424/773 |
| 2009/0297492 A1 * | 12/2009 | Satoh et al. | 424/94.1 |

* cited by examiner

*Primary Examiner* — Qiuwen Mi
(74) *Attorney, Agent, or Firm* — Nancy Lord, Ltd.; Don D. Cha

(57) ABSTRACT

A new composition and method are described for male fertility therapy. In one alternative, the composition utilizes three nutritional supplements, *Lepidium meyenii*, L-carnitine, and Coenzyme Q10. When it is administered to males as fertility therapy following the recommended therapeutic regimen, enhanced sperm count, sperm quality, and sperm motility results.

9 Claims, No Drawings

COMPOSITION AND METHOD FOR FERTILITY THERAPY USING NUTRITIONAL SUPPLEMENTS

CROSS-REFERENCE TO RELATED APPLICATIONS

This application claims priority as a continuation-in-part from Ser. No. 12/551,465, filed Aug. 31, 2009.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO SEQUENCE LISTING, A TABLE, OR A COMPUTER PROGRAM LISTING COMPACT DISK APPENDIX

Not Applicable

FIELD OF INVENTION

This invention is directed to fertility-enhancing dietary and nutritional supplement compositions for human male infertility therapy and to methods employing these compositions. By providing these supplements, the invention will provide a sperm count enhancing dose of *Lepidium meyenii*, a sperm quality enhancing dose of carnitine, and a sperm motility enhancing dose of Coenzyme Q10. The invention will provide, unlike others, a continued regimen of supplements that will provide the reproductive system with a continued supply of these nutrients, where in the body will manufacture certain agents that will boost the reproductive system and will assist the user to attain conception within a few months.

BACKGROUND OF THE INVENTION

An estimated six percent of adult males are thought to be infertile. Infertility is defined by most authorities as the inability to achieve a pregnancy after one year of unprotected intercourse. Conception is normally achieved within 12 months in 80-85 percent of couples using nocontraceptive measures; thus an estimated 15 percent of couples attempting their first pregnancy will have difficulty conceiving. While certain cases of male infertility are due to anatomical abnormalities such as varicoceles, ductal obstructions, or ejaculatory disorders, an estimated 40-90 percent of cases are due to deficient sperm production of unidentifiable origin. Sinclair, S, 5(1) Alt Med Review 28-38 (2000).

A normal semen sample should have a volume of 1.5-5.0 ml, with greater than 20 million sperm/ml. The number of abnormal sperm should be less than 40 percent, with greater than 30 percent of the sperm sample demonstrating proper motility. Unfortunately, conventional semen analysis is not a highly accurate predictor of fertility. Id. Approximately 30% of cases of couple infertility are due to a male factor. Several conditions can interfere with spermatogenesis and reduce sperm quality and production. Treatable conditions, such as hypogonadism, varicocele, infections and obstructions, should be diagnosed and corrected, but many aspects of male factor infertility remain unclear. Isidori, A M, et al, 12(6) Reprod Biomed Online 704-14 (2006).

Fifty two percent (52%) of men with a sperm count below 20 million/ml were able to impregnate their partners and 40 percent of men with a sperm count below 10 million/ml were also able to conceive. Conventional semen analysis often fails to identify infertile males with "normal" samples and conversely fails to identify fertile males with subnormal semen parameters. Another confounding factor is variations in sperm density, motility, and morphology among multiple samples from the same subject. Sinclair, S, 5(1) Alt Med Review 28-38 (2000). There is a growing body of scientific evidence supporting the idea that sperm counts have declined considerably over the last 50 years. Three recent reports also found semen quality has declined among donors over the last 20 years. Because the decline in sperm production is relatively recent, one must suspect a combination of environmental, lifestyle, and dietary factors might be interfering with spermatogenesis. Sinclair, S, 5(1) Alt Med Review 28-38 (2000).

Oxidative stress has been shown to be a major cause of male infertility; a large proportion of infertile men have elevated levels of seminal reactive oxygen species (ROS). High concentrations of ROS cause sperm pathology such as ATP depletion leading to insufficient axonemal phosphorylation, lipid peroxidation and loss of motility and viability. L-carnitine, a naturally occurring enzymatic antioxidant, is a necessary factor in the utilization of long chain fatty acids to produce energy. Dokmeci, D, 47(1) Folia Med (Plovdiv) 26-30 (2005).

Nutritional therapies have included L-carnitine, coenzyme Q10, L-arginine, zinc, and anti-oxidant vitamins such as Vitamin E, Vitamin C, Vitamin B12, glutathione and selenium.

Only a few published teachings claim to affect this serious and prevalent problem in the population through intervention in the nutritional status of patients. U.S. Patent Application No. 20070104801, to Cecchi, teaches an undescribed fertility enhancing and anti-aging composition that may contain any of alpha-lipoic acid, glucosamine sulfate or Peruvian Maca with or without horny goat weed.

U.S. Pat. No. 7,115,650, to Broqua, teaches a method of improving fertility by the administration of an inhibitor of dipeptidyl peptidase IV, wherein said inhibitor is an aminoacyl pyrrolidine or an amino-acyl thiazolidine.

U.S. Pat. No. 6,569,857, to Hermelin, teaches a method for increasing the possibility of conception while enhancing nutritional stores for a developing embryo or fetus prior to and during pregnancy by administering to an animal during a period commencing prior to at least two weeks before conception a specific dose of vitamin B6 and folic acid.

U.S. Pat. No. 7,410,657, to Lee, teaches several compositions for enhancing fertility that require a large number of herbs used in Chinese medicine, including *Radix Polygalae Tenuifoliae*, Semen *Ziziphi Spinosae*, *Radix Ginseng*, *Rhizoma Atractylodis* Macrocephalae, *Rhizoma Zingiberis* Officinalis Recens, *Sclerotium Poriae* Cocos, *Radix Astragali*, *Radix Ligustici Wallichii*, *Radix Angelicae Sinensis*, and the like.

U.S. Pat. No. 6,989,164, to Trant, teaches a pharmaceutical composition for oral ingestion having fertility promoting activity in males comprising components present in the proportion in parts by weight of: about 5 to 50% green tea, vitamin C, vitamin E, and selenium, about 10 to 80% L-carnitine, up to about 1% ferulic acid in Dong quai, up to about 1% vitamins B6, B12, and folate, up to about 10% zinc. The combination of L-carnitine and Coenzyme Q10, but not *Lepidium Meyenii*, is taught by another patent to Trant, U.S. Pat.

No. 7,045,151 for a pharmaceutical composition having fertility promoting activity in males comprising components present in the proportion in parts by weight of about 20 to 80% L-carnitine, about 5 to 30% vitamins C and E, about 0.1 to 10% coenzyme Q10, about 0.001 to 1% selenium, about 0.2 to 20% ferulic acid, about 0.1 to 2% zinc, and about 0.001 to 1% B vitamins.

U.S. Pat. No. 6,861,079, to Sweazy, teaches a fertility kit to enhance natural fertility and detect female ovulation and male fertility potential comprising specific dose ranges of L-Arginine, L-Cysteine, Selenium, Vitamin C, Vitamin E, Zinc, Astragalus, Pycnogenol, Vitamin B-6, Para-aminobenzoic acid (PABA), Vitamin A, Folic Acid, at least one phytoestrogen, along with several devices used in the promotion of ovulation timing and intercourse.

This inventor has discovered the elegant combination of these three nutrients, each with a primary effect on a different aspect of the sperm parameters.

*Lepidium Meyenii*

*Lepidium meyenii* (Brassicaceae), known as Maca, is a Peruvian hypocotyl that grows exclusively between 4000 and 4500 meters above sea level in the central Andes. Maca is traditionally employed in the Andean region for its supposed fertility-enhancing properties. A study aimed to test the hypothesis that different ecotypes of Maca (Red, Yellow and Black) after short-term (7 days) and long-term (42 days) treatment affect differentially spermatogenesis adult rats. Daily sperm production (DSP) was increased in the group treated with Black Maca compared with control values (P<0.05). Red or Yellow Maca did not alter DSP and epididymal sperm motility was not affected by treatment with any ecotype of Maca. After 42 days of treatment, Black Maca was the only ecotype that enhanced DSP (P<0.05). Moreover, Black Maca was the only that increased epididymal sperm motility (P<0.05). Black Maca appeared to have more beneficial effect on sperm counts and epididymal sperm motility. Gonzales, C, et al., 103(3) J. Ethnopharmacol. 448-54. Epub 2005 Sep. 19 (2006).

In spite of its historical use in the Andes, *Lepidium meyenii* has yet to be studied rigorously in infertile human males. Studies in the male rat have suggested the strong effect on sperm count. *Lepidium meyenii* was shown to improve sperm morphology and concentration, respectively, in uncontrolled trials in 2003. Comhaire F H, Mahmoud A, 7(4) Reprod Biomed Online 385-91 (2003). Yellow Maca has also been shown to enhance the fertility of female mice, by increases in the litter size and the uterine weight in ovariectomized animals. Ruiz-Luna, AC, et al, 3 Reprod Biol Endocrinol 3:16 (2005).

Male rats were treated by gavage with aqueous extract of each variety of maca equivalent to 1 g hypocotyl kg (−1) body weight (BW) for 84 days. At the end of the treatment, daily sperm production (DSP), epididymal sperm count (ESC) and sperm count in vas deferens (SCVD) were assessed. In addition, testis DNA quantification was determined. Any toxic effect was assessed in liver and spleen by histological studies. The results indicated that Yellow Maca and Black Maca improved ESC and that three varieties of maca increased the SCVD without affecting DSP. Moreover, testis DNA levels were not affected by treatment with any of the three varieties of maca. Maca seems to act as a modulator of sperm count at the reproductive tract level. Gasco, M, et al, 39(4) Andrologia. 151-8 (2007). In a study of Holtzman rats, epididymal sperm count was increased with 48 mg/day of Maca at all times. With 96 mg/day an increase in sperm count was observed at day 7, but it was reduced at day 14 and day 21 of treatment with affect on serum testosterone levels. Gonzales, G F, et al, 5(4) Asian J Androl 349-52 (2003).

In 2008, different extractions of the Black maca were studied in forty two adult male rats. Hydroalcoholic extract of Black Maca was partitioned with the following solvents: petroleum ether, chloroform, ethyl acetate, n-butanol, and water to obtain each fraction that were given orally by gavage for 7 days. Daily sperm production, epididymal sperm count, and sperm count in the vas deferens was measured. Daily sperm production was higher in the ethyl acetate group compared with all other groups. The epididymal sperm count was higher in rats treated with ethyl acetate fraction compared with rats treated with vehicle (control), petroleum ether, n-butanol, or water fractions. The sperm count in vas deferens was lower in rats treated with ethyl acetate, petroleum ether, or water fractions compared with the control group; thus, the sperm count in vas deferens in rats treated with chloroform and n-butanol fractions was higher than in the petroleum ether group. The greatest effect on spermatogenesis was observed in the ethyl acetate fraction from the hydroalcoholic extract of Black Maca, suggesting that the compounds related to the beneficial effect on sperm production of Black Maca are presented in this fraction. Yucra, S et al, 89(5 Suppl) Fertil Steril 1461-7. Epub 2007 (2008).

Aqueous extract of Black maca was given orally by daily gavage at a dose of 2 g kg (−1) to rats. In a spermatogenic cycle, compared with day 1, daily sperm production (DSP) was lower at day 7 (control), whereas with Black maca, the difference was observed at day 12. Epididymal sperm count was higher in rats treated with Black maca at days 1, 3 and 7, but similar to controls at days 5 and 12; similarly sperm counts in vas deferens was higher in rats treated with Black maca in days 3, 5 and 7, but similar to controls at days 1 and 12. From this, it is suggested that first action of Black maca was at epididymal level increasing sperm count after 1 day of treatment, whereas an increase in sperm count was observed in vas deferens at day 3 of treatment. Finally, an increase in DSP was observed after 7 days of treatment with Black maca. Gonzales, G F, et al, 38(5) Andrologia 166-72 (2006).

A dose-response study performed to determine the effect of 7 days oral administration of an aqueous lyophilized extract of Maca at 0.01-5 g/kg (corresponding to 0.022-11 g dry hypocotyls of Maca/kg) on body and different organ weights, stages of the seminiferous tubules, epididymal sperm count and motility, and serum testosterone and estradiol levels in rats. In doses up to 5 g extract/kg, no toxicity was observed. Maca increased in length of stages VII-VIII of the seminiferous tubules in a dose-response fashion, with highest response at 1.0 g/kg, while caput/corpus epididymal sperm count increased at the 1.0 g dose. Increase in epididymal sperm count was related to lengths of stages VII-VIII. Highest effect on stages VII-VIII of the seminiferous tubules was observed at 1.0 g Maca aqueous extract/kg. The study demonstrated that Maca extract in doses up to 5 g/kg (equivalent to the intake of 770 g hypocotyls in a man of 70 kg) was safe and that higher effect on reproductive parameters was elicited with a dose of 1 g extract/kg corresponding to 2.2 g dry Maca hypocotyls/kg. Chung, F, et al, 98(1-2) J Ethnopharmacol 143-7 (2005).

In another study of male rats given 666.6 mg/day of an aqueous extract of Maca hypocotyl for 21 days at high altitude, Maca increased the sperm count on day 21 of exposure to high altitude to values similar ($1095.25 +/- 20.41 \times 10(6)$ sperm, means+/−S.E.M.) to those obtained in the Maca-treated group at sea level ($1132.30 +/- 172.95 \times 10(6)$ sperm). Furthermore, in the Maca treated group exposed for 21 days to high altitude, epididymal sperm count was higher than in the non-treated group at sea level (690.49+/−43.67×10(6) sperm). Gonzales, G F, 180(1) J Endocrinol 87-95 (2004).

In one reported human study designed to determine the effect of a 4-month oral treatment with tablets of *Lepidium meyenii* (Maca) on seminal analysis in nine adult normal men aged 24-44 years old, nine men received tablets of Maca (1500 or 3000 mg/day) for 4 months. Seminal analysis was performed according to guidelines of the World Health Organization (WHO). Serum luteinizing hormone (LH), follicle stimulating hormone (FSH), prolactin (PRL), testosterone (T) and estradiol (E2) were measured before and after treatment. Treatment with Maca resulted in increased seminal volume, sperm count per ejaculum, motile sperm count, and sperm motility. Serum hormone levels were not modified with Maca treatment. Increase of sperm count was not related to dose of Maca. Maca improved sperm production and sperm motility by mechanisms not related to LH, FSH, PRL, T and E2. Gonzales, G F, 3(4) Asian J Androl 301-3 (2001). The lack of androgenic activity was also documented in other reports in normal human males, Gonzales, G F, 176(1) J Endocrinol 163-8 (2003) and in in-vitro analysis. Bogani, P, et al, 104(3) J Ethnopharmacol 415-7. Epub 2005 Oct. 18 (2006).

Carnitine

L-carnitine is an essential cofactor for mitochondrial, beta-oxidation of long-chain fatty acids, and is known to play important roles in sperm maturation and metabolism when spermatozoa pass and acquire motility in the epididymis. Azoospermia occurred in the epididymis in the juvenile visceral steatosis (JVS) mice, which are OCTN2 dysfunction mice caused by mutations in the gene encoding OCTN2, have been used for animal models of primary systemic carnitine deficiency. Animals used in this study were wild-type (C57BL/6 J) mice (n=4) and JVS mice (n=4). As measured by polyclonal antibodies, OCTN2 was localized on the apical membrane of the principal cells of distal corpus and cauda epididymides. These results suggest that OCTN2 functions as a carnitine transporter between the epithelium and the lumen in distal corpus and cauda epididymides and provides a clue as to why obstructive azoospermia is induced in distal parts of epididymis. Yakushiji K, et al, 13(4) Int J Urol 420-6 (2006).

The benefits of one of the components, carnitine, most specifically L-carnitine, of this invention in improving sperm quality is well-studied, Ng, C M, et al, 1033 Ann N Y Acad Sci 177-88 (2004), and may also improve sperm motility, Garolla, A, et al, 83(2) Fertil Steril 355-61 (2005). Spermatozoan maturation, motility, and fertility are, in part, dependent upon the progressive increase in epididymal and spermatozoal carnitine, critical for mitochondrial fatty acid oxidation, as sperm pass from the caput to the cauda of the epididymis. The organic cation/carnitine transporters, OCTN1, OCTN2, and OCTN3, are expressed in sperm as three distinct proteins with an expected molecular mass of 63 kDa, using Western blot analysis and our transporter-specific antibodies. Xuan, W, et al, 306(1) Biochem Biophys Res Commun 121-8 (2003). The gene products OCTN2 and OCTN3 transport carnitine with high affinity, are both expressed in testis, where carnitine is required to maintain sperm cell motility. Maeda, T, et al, 70(6) Biochem Pharmacol. 858-68 (2005). Defective sperm carnitine transport may be a potentially treatable etiologies of male infertility, responsive to L-carnitine supplementation.

Some studies have shown carnitine levels and supplementation to correlate with numerous parameters of sperm function. In a study of 170 infertile men who received either L-carnitine 1 g/day or acetyl-L-carnitine 500 mg/day for six months, there was a significant correlation between seminal carnitine concentration and sperm concentration, total sperm count, sperm total motility, rapid forward progression, live sperm count, membrane function, nuclear DNA integrity, capacity for cervical mucus penetration, linearity of spermatic movement, and amplitude of lateral sperm head movement (all p<0.0001) in the entire study population. De Rosa, M, et al, 6(1) Drugs R D 1-9 (2005).

In a study of 64 infertile men, the Pearson coefficients of correlation of the levocarnitine level with sperm motility, vitality and concentration were 0.161 (P=0.235), 0.114 (P=0.370) and 0.637 (P<0.001), those of free seminal carnitine with sperm motility and vitality were 0.325 (P=0.024) and 0.316 (P=0.029), respectively, with the oligozoospermia group excluded, and that of partial correlation between the concentrations of seminal levocarnitine and sperm was 0.641 (P<0.001). The authors concluded that the level of seminal plasma levocarnitine was positively correlated with sperm motility and vitality, and more significantly with sperm concentration. Tang, L F, et al, 14(8) Zhonghua Nan Ke Xue 704-8 (2008).

Other groups have shown carnitine levels to be more closely associated with sperm quality than other sperm parameters. Lenzi, A, et al, 79(2) Fertil Steril (2003) stated that larger clinical studies were appropriate, confirmed the suggestions of the Xuan group in a two month cross-over design comparing 2 g/day carnitine to placebo with a 2 month washout. One hundred young (20-40) infertile patients with defects in concentration, total motility, forward motility, atypical forms and micro/s linearity were studied of whom eighty six (86) completed the study. At the conclusion of both cycles, variation in sperm parameters used in the patients selection was measured in particular, sperm motility. However, excluding outliers, a statistically significant improvement in semen quality over placebo was seen after the L-carnitine therapy; specifically in concentration and both total and forward motility. The later was more significant in those patients with lower initial values, i.e., <5×10(6) or <2×10(6) of forward motile sperm/ejaculate or sperm/mL. The authors concluded that based on a controlled study of efficacy, L-carnitine therapy was effective in increasing semen quality, especially in groups with lower baseline levels.

In a meta-analysis of nine randomized clinical trials, administration of L-carnitine or acetyl-L-carnitine therapy compared to placebo showed significant improvement in pregnancy rate (OR=4.10, 95% CI (2.08, 8.08), p<0.0001), total sperm motility (WMD=7.43, 95% CI (1.72, 13.14), p=0.04, forward sperm motility (WMD=11.83, 95% CI (0.49, 23.16), p=0.04) and atypical sperm cell (WMD=−5.72, 95% CI (−7.89, −3.56), p<0.00001) without significant difference was found in the sperm concentration (WMD=5.69, 95% CI (−4.47, 15.84), p=0.27) and semen volume (WMD=0.28, 95% CI (−0.02, 0.58), p=0.07). The authors concluded that LC and/or LAC may be effective in improving pregnancy rate and sperm kinetic features in patients affected by male infertility. Zhou X, Liu F, Zhai S. 16 Suppl 1 Asia Pac J Clin Nutr 383-90 (2007). Other groups, however, have shown levels of free L-carnitine in the seminal plasma of the fertile men to be significantly higher than that of the infertile (P<0.01). The lower the sperm concentration, the weaker the sperm vitality, the more significant the difference. The level of free L-carnitine in the semen was positively correlated with sperm concentration R=0.521, P<0.001), and sperm motility R=0.319, P<0.001) and vitality R=0.251, P<0.001). Li, K, 13(2) Zhonghua Nan Ke Xue:143-6 (2007).

In a study of patients with oligoasthenospermia, 90 patients were given L-carnitine (2 g/d) and acetyl-L-carnitine (1 g/d) orally, twice a day and compared to 60 patients in the control group were given Vitamin E 100 mg plus Vitamin C 100 mg, tid for three months. Sperm analysis was performed monthly. In the treatment group, 85 patients out of 90 finished the three month treatment. Female spouses of 10 patients (11.6%) achieved pregnancy. Moreover, their forward motile sperm per ejaculation, total motile sperm, as well as the concentration of L-carnitine in seminal plasma were increased significantly (P<0.01). In control group, 53 patients out of 60 completed three months therapy. Two pregnancy (3.7%) was observed. Though some increase was seen in number of forward motile sperm and total motile sperm per ejaculation, the changes were not statistically significant (P>0.05). The difference of the pregnancy rate between two groups was statistically significant. Li, Z, et al, 11(10) Zhonghua Nan Ke Xue 761-4 (2005).

Sixty patients with idiopathic asthenospermia underwent a double-blind therapy of L-carnitine (LC) 3 g/d, L-acetyl-carnitine 3 g/d (LAC), a combination of both, or placebo for 6 months preceded by a one month wash-out and evaluated at 3 months of treatment. Sperm cell motility increased in patients to whom LAC was administered both alone or in combination with LC; combined LC+LAC therapy led to a significant improvement of straight progressive velocity after 3 months. The total oxyradical scavenging capacity of the semen toward hydroxyl and peroxyl radicals also increased and was positively correlated with the improvement of kinetic features. Patients with lower baseline values of motility and total oxyradical scavenging capacity of the seminal fluid had a significantly higher probability of responding to the treatment. Balercia, G, et al, 84(3) Fertil Steril 662-71 (2005).

Reports are not consistent in regards to the effects of carnitine on sperm parameters. In a smaller study of twenty-one patients with idiopathic asthenospermia, 12 treated with carnitine and 9 with placebo, there were no significant differences in baseline semen parameters between the carnitine and placebo arms, or in motility or total motile sperm counts between baseline, 12 week, or 24 weeks in the carnitine or placebo. Sigman, M, et al, 85(5) Fertil Steril. 1409-14. Epub 2006.

Patients with inflammatory abacterial prostatovesiculoepididymitis (PVE) were shown to benefit from carnitine supplementation. In an open label study, carnitines (group A; n=30) or nonsteroidal anti-inflammatory drugs (group B; n=16) for 4 months; nonsteroidal anti-inflammatory drugs for 2 months, followed by treatment with carnitines for 2 months (group C; n=26); or nonsteroidal anti-inflammatory treatment given concomitantly with carnitines (group D; n=26) for 4 months. Following a 3-month washout period, patients in the group that had received only carnitine (group C) had the highest reduction in production of reactive oxygen species associated with increased sperm motility and viability and the group that had received only nonsteroidal anti-inflammatory drugs experienced the least effect. Vicari, E, 73(1) Arch Ital Urol Androl 15-25 (2001).

Seminal plasma total carnitine concentrations were determined in 79 men. The seminal plasma of 65 infertile men and 14 men as a control group with proved fertility were investigated. The concentrations of total carnitine were reduced significantly in the infertile group compared to the control group (P<0.05>. When the 65 infertile men were divided into five groups according to their sperm analysis: normospermia (n=42), oligospermia (n=23), asthenospermia (n=40), teratospermia (n=44) and oligoasthenospermia (n=10), there was a statistically significant positive correlation between seminal plasma total carnitine concentration with total sperm count and the percentage of normal forms (P<0.05 and P<0.01, respectively). Total carnitine concentration was found to be low in the asthenospermia group when compared with the group of patients, whose total motile sperm percentage was 51 (P<0.05). Gürbüz, B, et al, 23(6) J Obstet Gynaecol. 653-6 (2003).

The main function of carnitine is in the epididymis is to provide an energetic substrate for spermatozoa. Carnitine contributes directly to sperm motility and may be involved in the successful maturation of sperm. This especially important since epididymal sperm use fatty acid oxidation as their main source of energy metabolism, and thus tend to concentrate carnitine while in the epididymis, as carnitine is necessary for transport of fatty acids into the mitochondria. Low levels of carnitine reduce fatty acid concentrations within the mitochondria, leading to decreased energy production and potential alterations in sperm motility. In a study involving 124 infertile patients, a direct correlation between semen carnitine content and sperm motility was found, Sinclair, S, 5(1) Alt Med Review 28-38 (2000).

Coenzyme Q10

Coenzyme Q10 has been shown by several researchers to improve sperm motility. It is concentrated in the mitochondrial mid-piece, where it is involved in energy production. It also functions as an antioxidant, preventing lipid peroxidation of sperm membranes. When sperm samples from 22 asthenospermic men were incubated in vitro with 50 microM Coenzyme Q10, significant increases in motility were observed. Coenzyme Q10 (60 mg) was given to 17 infertile patients for a mean 103 days, and although there were no significant changes in standard sperm parameters, there was a significant improvement in fertilization rate (p<0.05). Sinclair, S, 5(1) Alt Med Review 28-38 (2000).

Early reports of the relationship and effects of coenzyme Q10 concentration and seminal fluid pathology, linked to infertility, varied. In a 1994 study, Coenzye Q10 was assayed in total seminal fluid (in 60 patients), in seminal plasma (in 44 patients), or in both seminal fluid and seminal plasma (in 27 patients). These authors showed significant correlations (higher Co Q10 with better parameters) in both sperm count and motility. When considering the total sample, there was a significant correlation between Coenzyme Q10 values and sperm Count®=0.504, P<0.0005). A significant correlation was also found between Coenzyme Q10 value and the percent of total motile Forms®=0.261, P<0.05). Different Coenzyme Q10 concentrations were also observed in subjects with normal (>40%, n=35) or altered (<40%, n 25) sperm motility (0.28±0.03 mcg/ml vs. 0.19±0.02 mcg/ml, P<0.05). Varicocele patients had the correlation with count but not motility. Mancini, A, et al, 15(6) J Androl 591-4 (1994).

Other authors reported, however, an increase in Coenzyme Q10 in the semen of infertile men and postulate that the large difference in Coenzyme Q10, concentration between the fertile and infertile population could result from either a greater uptake or a reduced consumption of ATP, the essential energy reserve for all of the cells in the body. Noting that as cell population numbers increase, ATP use increases and circulating Coenzyme Q10 levels drop, possibly explaining this phenomenon in semen. Angelitti, A G, et al, 41(2) Clin Chem 217-219 (1995).

More recent studies have not all demonstrated the correlations that those observed by Angelita and his colleagues in 1995. Mancini, A, et al, 30(1) Andrologia. 1-4 (1998) noted that the previously reported correlation with sperm motility was lacking only in patients with varicocele, and a higher proportion of Coenzyme Q10 was found in the seminal plasma of varicocele patients. Like Angelita, this group observed that a higher concentration of Coenzyme Q10 (expressed as ng of the molecule per million of cells) was present in the spermatozoa of oligospermic and asthenospermic patients (sperm count<20×10(6) spermatozoa ml-1, sperm motility<40%) only in non-varicocele patients. This relationship was not observed in varicocele subjects, who also showed slightly lower intracellular absolute values of the coenzyme. The authors postulated that since Coenzyme Q10 is an antioxidant molecule involved in the defense of the cell from free radical damage, higher intracellular concentrations may represent a mechanism of protection of the spermatozoa in non-varicocele but not in varicocele patients.

Dramatic results in improving sperm motility were reported by Lewin A, Lavon H, 18 Suppl Mol Aspects Med: S213-9 (1997). To evaluate the effect of Coenzyme Q10 on sperm motility in vitro, after incubation with 38 samples of asthenospermic and normal motility sperm, and the effect of Coenzyme Q10 administration in vivo in 17 patients with low fertilization rates after in vitro fertilization with intracytoplasmic sperm injection (ICSI) for male factor infertility, sperm samples were divided and incubated for 24 h in: HAM's medium alone, in HAM's medium with 1% DMSO and HAM's with 5 microM or 50 microM Coenzyme Q10. While no significant change in motility after incubation was observed in the samples with initial normal motility, a significant increase in motility was observed in the 50 microM Coenzyme Q10 subgroup of sperm from asthenospermic men, with a motility rate of 35.7+/−19.5%, as compared to 19.1+/−9.3% in the controls (P<0.05).

The reduction state of Coenzyme Q10 in seminal fluid was also investigated. After the first in vitro experiments Coenzyme Q10 was administered to a group of idiopathic asthenozoospermic infertile patients, seminal analysis showed a significant increase of Coenzyme Q10 both in seminal plasma and in sperm cells, together with an improvement in sperm motility. The increased concentration of Coenzyme Q10 in seminal plasma and sperm cells, the improvement of semen kinetic features after treatment, and the evidence of a direct correlation between Coenzyme Q10 concentrations and sperm motility strongly supported a causative relationship. Mancini, A, et al, 25(1-4) Biofactors 165-74 (2005).

In another study, Infertile men with idiopathic asthenozoospermia were administered Coenzyme Q10 orally and semen samples were collected at baseline and after 6 months of therapy. Coenzme Q10 levels increased significantly in seminal plasma and in sperm cells after treatment and a significant increase was also found in sperm cell motility as confirmed by computer-assisted analysis. This was believed by the authors to be the result of its role in mitochondrial bioenergetics and its antioxidant properties. Balercia, G, et al, 81(1) Fertil Steril:93-8 (2004).

SUMMARY OF INVENTION

Pursuant to this invention a new composition and method is described to provide human male infertility therapy.

DETAILED DESCRIPTION OF THE PREFERRED EMBODIMENTS

The present invention describes an alternative therapy for infertility. The effects of the three nutrient components of this composition have been shown by various researchers, but never before has a composition been provided that offers the combined effects of a sperm count enhancing dose of *Lepidium meyenii*, a sperm quality enhancing dose of carnitine, and a sperm motility enhancing dose of Coenzyme Q10.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In the Summary above, the Description of the Invention, and the Claims and Abstract below, reference may be made to particular features (including method steps) of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "or" is used herein as a conjunction used to link alternatives in a series of alternatives. The term "and/or" is used herein as a conjunction meaning that either or both of two options may be valid.

"Animal" refers to a human, mammal or any other animal. "Conception" refers to the beginning of pregnancy as marked by the formation of a zygote. "Possibility of conception" refers to the likelihood of conception occurring during normal sexual activity. "Nutritional stores" refers to the levels of vitamins, minerals and other nutrients which will be available for use by the father, mother, developing embryo, fetus and newborn infant. "Nutritional status" refers to the presence or absence of any vitamin or mineral deficiency, or in other words, the extent to which physiological vitamin and mineral demands are being satisfied such that deficiency is avoided.

"Normospermia" refers to the production of spermatozoa normal in number and motility. "Oligospermia" refers to the production of fewer sperm than normal. "Asthenospermia" refers to the loss or reduction of spermatozoan motility. "Azoospermia" refers to the production of no sperm at all. "Teratospermia" refers to the production of malformed spermatozoa in the semen. "Oligoasthenospermia" refers to the production of fewer sperm than normal with decreased motility. "Sperm count" refers to the number of sperm counted in a standard volume of semen; "Sperm quality" refers to the percentage of viable sperm and the morphology (shape) of the sperm; and Sperm motility refers to the measurement of the sperms ability to "swim" through a volume, usually in a forward direction.

In the one embodiment of this invention, a fertility-enhancing composition for human male fertility therapy is taught, comprising a sperm count enhancing dose of *Lepidium meyenii*, a sperm quality enhancing dose of carnitine, and a sperm motility enhancing dose of Coenzyme Q10. The composition may be is in a dosage form of a tablet, capsule, liquid, liposome, inhalant, sublingual tablet, suppository, oral spray and dermal patch and may further comprise a pharmaceutically acceptable carrier.

In a more specific embodiment, the *Lepidium meyennii* is present in amount of about 80 mg to about 8 gm, the carnitine is present in an amount of 10 mg to about 1000 mg, and the Coenzyme Q10 is present in an amount of about 1 mg to about 150 mg.

In an even more specific embodiment, the *Lepidium meyennii* is present in amount of about 250 mg to about 2500 gm, the carnitine is present in an amount of 40 mg to about 400 mg of carnitine, and the Coenzyme Q10 is present in an amount of about 3 mg to about 50 mg. Most specifically, the *Lepidium meyennii* is present in amount of about 800 mg, the carnitine is present in an amount of about 125 mg, and the Coenzyme Q10 is present in an amount of about 15 mg. The *Lepidium Meyenii* may be is present in the form of a 4:1 extract of *Lepidium meyenii* root, or an extract of the hypocotyl, and said carnitine may be L-carnitine or acetyl L-carnitine.

The fertility-enhancing composition may comprise at least of one additional nutrient selected from the group consisting of grape seed, and ginseng. More specifically, the grape seed may contain 90% proanthocyanidins and be present in an amount of about 10 mg to about 1000 mg and the ginseng may be panax ginseng and present in an amount of about 10 mg to about 1000 mg. Even more specifically, the grape seed is present in an amount of about 30 mg to about 300 mg and the panax ginseng is present in an amount of amount of about 30 mg to about 300 mg. Most specifically, the grape seed is present in an amount of about 100 mg and the panax ginseng is present in an amount of about 100 mg.

The fertility-enhancing composition may further comprise a multi-vitamin comprising Vitamin A, Vitamin C, Vitamin D3, Vitamin E, Vitamin K, thiamine, Riboflavin, Niacin, Vitamin B6, Folic Acid, Vitamin B12, Pantothenic Acid, Iodine, Magnesium, Zinc, Selenium, Copper, Manganese, and Chromium. More specifically, the Vitamin A is beta carotene in an amount of about 15 mg, the Vitamin C is ascorbic acid in an amount of about 250 mg, the Vitamin D3 is cholicalciferol in an amount of about 4 mg, the Vitamin E is d-alpha tocopheryl succinate in amount of about 150 mg, the Vitamin K is in an amount of 80 mcg, the thiamine is thiamine hydrochloride in an amount of about 1.5 mg, the riboflavin is in an amount of about 1.7 mg, the niacin is present in an amount of about 20 mg, the Vitamin B6 is pyridoxal 5'phosphate and is present in an amount of about 2 mg, the folic acid is present in an amount of about 500 mcg, the Vitamin B12 is methylcobalamin and is present in an amount of about 25 mcg, the pantothenic acid is from d-calcium pantothenate and is present in an amount of 10 mg, the iodine is from kelp and is present in an amount of about 150 mcg, the magnesium is magnesium oxide and is present in an amount of about 120 mg, the zinc is zinc gluconate and is present in an amount of about 30 mg, the selenium is selenomethionine and is present in an amount of about 100 mcg, the copper is copper gluconate and is present in an amount of about 2 mg, the manganese is manganese sulfate and is present in an amount of about 2 mg, the chromium is chromium polynicotinate and is present in an amount of about 120 mcg.

In yet another specific embodiment, the fertility-enhancing composition for male fertility therapy consists of about 80 mg to about 8 gm of *Lepidium meyennii*, about 10 mg to about 1000 mg of carnitine, about 1 mg to about 150 mg of Coenzyme Q10, about 10 mg to about 1000 mg of grape seed, about 5 mg to about 500 mg of ginseng, about 1 mg to about 150 mg Vitamin A, about 25 mg to about 2500 mg of Vitamin C, about 1 mg to about 40 mg of Vitamin D3, about 15 mg to about 1500 mg of Vitamin E, about 8 mcg to about 800 mcg of Vitamin K, about 0.2 mg to about 15 mg thiamine, about 2 mg to about 200 mg of niacin, about 0.2 mg to about 200 mg of Vitamin B6, about 50 mcg to about 5 mg of folic acid, about 2.5 mcg to about 250 mcg of Vitamin B12, about 1 mg to about 100 mg of pantothenic acid, about 1.5 mg to about 150 mg of iodine, about 20 mg to about 2000 mg of magnesium, about 10 mg to about 300 mg of zinc, about 10 mcg to about 1 mg of selenium, about 200 mcg to about 20 mg of copper, about 200 mcg to about 20 mg of manganese, and about 12 mcg to about 1.2 mg of chromium.

More specifically, the fertility-enhancing composition consists of about 250 mg to about 2500 mg of *Lepidium meyennii*, about 40 mg to about 400 mg of carnitine, about 3 mg to about 50 mg of Coenzyme Q10, about 30 mg to about 300 mg of grape seed, about 30 mg to about 300 mg of ginseng, about 5 mg to about 50 mg of Vitamin A, about 80 mg to about 750 mg of Vitamin C, about 1 mg to about 12 mg of Vitamin D3, about 50 mg to about 500 mg of Vitamin E, about 25 mcg to about 250 mcg of Vitamin K, about 0.5 mg to about 5 mg of thiamine, about 0.5 mg to about 5 mg of riboflavin, about 6 mg to about 60 mg of niacin, about 1 mg to about 6 mg of Vitamin B6, about 1.5 mg to about 250 mcg to about 1.5 mg of folic acid, about 8 mcg mg to about 800 mcg of Vitamin B12, about 3 mg to about 30 mg of pantothenic acid, about 5 mg to about 50 mg of iodine, about 60 mg to about 600 mg of magnesium, about 30 mg to about 90 mg of zinc, about 30 mcg to about 300 mcg of selenium, about 600 mcg to about 6 mg of copper, about 600 mcg to about 6 mg of manganese, and about 40 mcg to about 400 mcg of chromium.

In its most specific embodiment, the fertility-enhancing composition consists of about 800 mg of *Lepidium meyennii*, present as a 4:1 root extract, about 125 mg of carnitine, about 15 mg of Coenzyme Q10, about 100 mg of grape seed with 90% proanthocyanidins, about 100 mg of ginseng present as panax ginseng with 5% ginsenosides, about 15 mg of Vitamin A present as beta carotene, about 250 mg of Vitamin C present as ascorbic acid, about 4 mg of Vitamin D3 present as cholicalciferol, about 150 mg of Vitamin E present as d-alpha tocopheryl succinate, about 80 mcg of Vitamin K, about 1.5 mg of thiamine, about 1.7 mg of riboflavin, about 20 mg of niacin, about 2 mg of Vitamin B6 present as pyridoxal 5'phosphate, about 500 mcg of folic acid, about 25 mcg of Vitamin B12 present as methylcobalamin, about 10 mg of pantothenic acid, about 150 mcg of iodine from kelp, about 120 mg of magnesium present as magnesium oxide, about 30 mg of zinc present as zinc gluconate, about 100 mcg of selenium present as selenomethionine, about 2 mg of copper present as copper gluconate, about 2 mg of manganese present as manganese.

Also taught is a method of enhancing fertility in a male human in need thereof by enhancing sperm count, sperm quality, and sperm motility comprising administering an effective amount of the composition of claim 1 to a patient in need of treatment thereof. The administration may be in one to three doses per day and is continued until conception is achieved by the female partner of said male human, or for at least 3 months. The method may further include the administration of an appropriate fertility enhancing composition to the female partner of the male human.

The invention is described by the following non-limiting example:

Example 1

Ninety patients with oligoasthenospermia, patients are orally administered *Lepidium Meyenii* at 800 mg, L-carnitine at 125 mg, and Coenzyme Q10 at 15 mg; ninety patients are orally administered placebo. Eighty of the 90 patients in the active treatment group and 75 of the controls finish the three month treatment period. At the end of the period, female spouses of 10 patients (12.5%) achieve pregnancy. Moreover, their forward motile sperm per ejaculation, total motile sperm, sperm count, and sperm quality parameters of vitality and morphology in seminal plasma is increased significantly ($P<0.01$). In control group, only two pregnancies, (2.6%) are observed. Though some increase was seen in number of forward motile sperm and total motile sperm per ejaculation, the changes are not statistically significant ($P>0.05$) in the control group and the difference of the pregnancy rate between two groups is statistically significant.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A fertility-enhancing composition for human male fertility therapy comprising:
    (i) a sperm count enhancing dose of *Lepidium meyenii*,
    (ii) a sperm quality enhancing dose of carnitine,
    (iii) a sperm motility enhancing dose of Coenzyme Q10,
    (iv) a multi-vitamin comprising Vitamin A, Vitamin C, Vitamin D3, Vitamin E, Vitamin K, thiamine, Riboflavin, Niacin, Vitamin B6, Folic Acid, Vitamin B 12, Pantothenic Acid,
    (v) Iodine,
    (vi) Magnesium,
    (vii) Zinc,
    (viii) Selenium,
    (ix) Copper,
    (x) Manganese,
    (xi) Chromium, and
    (xii) at least of one additional nutrient selected from the group consisting of grape seed, and ginseng.

2. The fertility enhancing composition of claim 1 wherein said Vitamin A is beta carotene in an amount of about 15 mg, said Vitamin C is ascorbic acid present in an amount of about 250 mg, said Vitamin D3 is cholicalciferol in an amount of about 4 mg, said Vitamin E is d-alpha tocopheryl succinate present in amount of about 150 mg, said Vitamin K is present in an amount of 80 mcg, said thiamine is thiamine hydrochloride and is present in an amount of about 1.5 mg, said riboflavin is present in an amount of about 1.7 mg, said niacin is present in an amount of about 20 mg, said Vitamin B6 is pyridoxal 5'-phosphate and is present in an amount of about 2 mg, said folic acid is present in an amount of about 500 mcg, said Vitamin B12 is methylcobalamin and is present in an amount of about 25 mcg, said pantothenic acid is from d-calcium pantothenate and is present in an amount of 10 mg, said iodine is from kelp and is present in an amount of about 150 mcg, said magnesium is present as magnesium oxide and is present in an amount of about 120 mg, said zinc is zinc gluconate and is present in an amount of about 30 mg, said selenium is selenomethionine and is present in an amount of about 100 mcg, said copper is copper gluconate and is present in an amount of about 2 mg, said manganese is manganese sulfate and is present in an amount of about 2 mg, said chromium is chromium polynicotinate and is present in an amount of about 120 mcg.

3. A fertility-enhancing composition for male fertility therapy consisting of about 80 mg to about 8 gm of *Lepidium Meyenii*, about 10 mg to about 1000 mg of carnitine, about 1 mg to about 150 mg of Coenzyme Q10, about 10 mg to about 1000 mg of grape seed, about 5 mg to about 500 mg of ginseng, about 1 mg to about 150 mg Vitamin A, about 25 mg to about 2500 mg of Vitamin C, about 1 mg to about 40 mg of Vitamin D3, about 15 mg to about 1500 mg of Vitamin E, about 8 mcg to about 800 mcg of Vitamin K, about 0.2 mg to about 15 mg thiamine, about 2 mg to about 200 mg of niacin, about 0.2 mg to about 200 mg of Vitamin B6, about 50 mcg to about 5 mg of folic acid, about 2.5 mcg to about 250 mcg of Vitamin B12, about 1 mg to about 100 mg of pantothenic acid, about 1.5 mg to about 150 mg of iodine, about 20 mg to about 2000 mg of magnesium, about 10 mg to about 300 mg of zinc, about 10 mcg to about 1 mg of selenium, about 200 mcg to about 20 mg of copper, about 200 mcg to about 20 mg of manganese, and about 12 mcg to about 1.2 mg of chromium.

4. The fertility-enhancing composition of claim 3 consisting of about 250 mg to about 2500 mg of *Lepidium Meyenii*, about 40 mg to about 400 mg of carnitine, about 3 mg to about 50 mg of Coenzyme Q10, about 30 mg to about 300 mg of grape seed, about 30 mg to about 300 mg of ginseng, about 5 mg to about 50 mg of Vitamin A, about 80 mg to about 750 mg of Vitamin C, about 1 mg to about 12 mg of Vitamin D3, about 50 mg to about 500 mg of Vitamin E, about 25 mcg to about 250 mcg of Vitamin K, about 0.5 mg to about 5 mg of thiamine, about 6 mg to about 60 mg of niacin, about 1 mg to about 6 mg of Vitamin B6, about 1.5 mg to about 250 mcg of folic acid, about 8 mcg to about 250 mcg of Vitamin B12, about 3 mg to about 30 mg of pantothenic acid, about 5 mg to about 50 mg of iodine, about 60 mg to about 600 mg of magnesium, about 30 mg to about 90 mg of zinc, about 30 mcg to about 300 mcg of selenium, about 600 mcg to about 6 mg of copper, about 600 mcg to about 6 mg of manganese, and about 40 mcg to about 400 mcg of chromium.

5. The fertility-enhancing composition of claim 4 consisting of about 800 mg of *Lepidium Meyenii*, present as a 4:1 root extract, about 125 mg of carnitine, about 15 mg of Coenzyme Q10, about 100 mg of grape seed with 90% proanthocyanidins, about 100 mg of ginseng present as panax ginseng with 5% ginsenosides, about 15 mg of Vitamin A present as beta carotene, about 250 mg of Vitamin C present as ascorbic acid, about 4 mg of Vitamin D3 present as cholicalciferol, about 150 mg of Vitamin E present as d-alpha tocopheryl succinate, about 80 mcg of Vitamin K, about 1.5 mg of thiamine, about 20 mg of niacin, about 2 mg of Vitamin B6 present as pyridoxal 5'-phosphate, about 500 mcg of folic acid, about 25 mcg of Vitamin B12 present as methylcobalamin, about 10 mg of pantothenic acid, about 150 mcg of iodine from kelp, about 120 mg of magnesium present as magnesium oxide, about 30 mg of zinc present as zinc gluconate, about 100 mcg of selenium present as selenomethionine, about 2 mg of copper present as copper gluconate, about 2 mg of manganese present as manganese.

6. A method of enhancing fertility in a male human in need thereof by enhancing sperm count, sperm quality, and sperm motility comprising administering an effective amount of the composition of claim 1 to a patient in need of treatment thereof.

7. The method of claim 6 wherein said male human has a female partner and said administration is in one to three doses per day and is continued until conception is achieved by the female partner of said male human.

8. The method of claim 7 wherein said administration is in one to three doses per day and is continued for at least 3 months.

9. The method of claim 8 wherein said female partner is administered an appropriate fertility enhancing composition for female fertility therapy.

* * * * *